US009326825B2

(12) United States Patent
Cleary et al.

(10) Patent No.: US 9,326,825 B2
(45) Date of Patent: May 3, 2016

(54) PATIENT MOUNTED MRI AND CT COMPATIBLE ROBOT FOR NEEDLE GUIDANCE IN INTERVENTIONAL PROCEDURES

(71) Applicant: CHILDREN'S NATIONAL MEDICAL CENTER, Washington, DC (US)

(72) Inventors: Kevin Cleary, Washington, DC (US);
Reza Monfaredi, Washington, DC (US);
Raymond Sze, Washington, DC (US);
Karun Sharma, Washington, DC (US);
Nabile Safdar, Washington, DC (US);
Reza Seifabadi, Washington, DC (US)

(73) Assignee: Children's National Medical Center, Washington (CO)

( * ) Notice: Subject to any disclaimer, the term of this patent is extended or adjusted under 35 U.S.C. 154(b) by 0 days.

(21) Appl. No.: 14/307,125

(22) Filed: Jun. 17, 2014

(65) Prior Publication Data
US 2014/0371584 A1    Dec. 18, 2014

Related U.S. Application Data

(60) Provisional application No. 61/835,654, filed on Jun. 17, 2013.

(51) Int. Cl.
*A61B 19/00* (2006.01)
*A61M 5/42* (2006.01)
(Continued)

(52) U.S. Cl.
CPC ............ *A61B 19/2203* (2013.01); *A61M 5/427* (2013.01); *A61M 5/46* (2013.01);
(Continued)

(58) Field of Classification Search
CPC ....................................................... B25J 9/107
See application file for complete search history.

(56) References Cited

U.S. PATENT DOCUMENTS 5,053,042 A   10/1991 Bidwell
5,320,111 A   6/1994 Livingston
(Continued)

FOREIGN PATENT DOCUMENTS

WO      WO 96/19944 A1    7/1996

OTHER PUBLICATIONS

Walsh et al, "A Patient-Mounted, Telerobotic Tool for CT-Guided Percutaneous Interventions" Journal of Medical Devices March 2008, vol. 2 / 011007-1-9.*

(Continued)

*Primary Examiner* — Amanda Lauritzen Moher
*Assistant Examiner* — Serkan Akar
(74) *Attorney, Agent, or Firm* — Oblon, McClelland, Maier & Neustadt, L.L.P.

(57) ABSTRACT

A patient mountable robot includes a four link mechanism, three actuators, and a first robot base. The mechanism includes four links that form a closed loop structure. The four links include a base link that includes a spherical joint. The mechanism provides two rotational degrees of freedom about the spherical joint for a needle that is configured to pass through the spherical joint. A first actuator is attached to the mechanism and moves the mechanism to provide the first of the two rotational degrees of freedom. A second actuator is attached to the mechanism and moves the mechanism to provide the second of the two rotational degrees of freedom. The base link of the mechanism passes through the first robot base. A third actuator is attached to the first robot base and linearly translates the base link so that a translational degree of freedom is provided for the needle.

16 Claims, 16 Drawing Sheets

(51) Int. Cl.
*A61M 5/46* (2006.01)
*A61B 17/34* (2006.01)

(52) U.S. Cl.
CPC ... *A61B2017/3407* (2013.01); *A61B 2019/524* (2013.01); *A61B 2019/5236* (2013.01); *Y10S 901/01* (2013.01)

(56) References Cited

U.S. PATENT DOCUMENTS

| | | | |
|---|---|---|---|
| 6,247,738 B1 | 6/2001 | Winkel et al. | |
| 6,379,307 B1 | 4/2002 | Filly et al. | |
| 6,497,548 B1 * | 12/2002 | Roy et al. | 414/735 |
| 6,546,279 B1 | 4/2003 | Bova et al. | |
| 7,950,306 B2 | 5/2011 | Stuart | |
| 2006/0058640 A1 * | 3/2006 | Cinquin et al. | 600/415 |
| 2007/0219031 A1 * | 9/2007 | Jones | 474/148 |
| 2009/0143907 A1 * | 6/2009 | Demathelin et al. | 700/245 |
| 2012/0265051 A1 | 10/2012 | Fischer et al. | |

OTHER PUBLICATIONS

Monfaredi, R. et al., "A Prototype Body-Mounted MRI-Compatible Robot for Needle Guidance in Shoulder Arthrography" 2014 5th IEEE RAS & EMBS International Conference on Biomedical Robotics and Biomechatronics (BioRob). Aug. 12-15, 2014; figure 2.
PCT International Search Report and Written Opinion issued Dec. 9, 2014 in PCT/US2014/042685 filed Jun. 17, 2014.

* cited by examiner

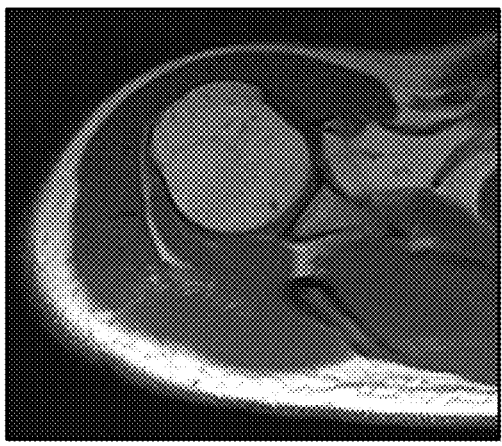 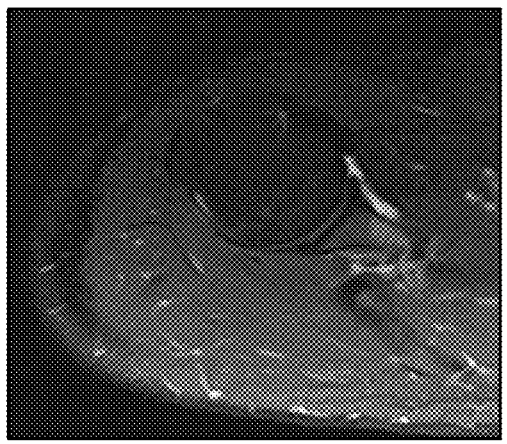
Fig. 26(A)                     Fig. 26(B)

PATIENT MOUNTED MRI AND CT COMPATIBLE ROBOT FOR NEEDLE GUIDANCE IN INTERVENTIONAL PROCEDURES

CROSS REFERENCE TO RELATED APPLICATION

This application is based upon and claims the benefit of priority from U.S. Provisional Patent Application No. 61/835,654, filed on Jun. 17, 2013, the entire contents of which are incorporated herein by reference.

BACKGROUND

I. Field of the Disclosure

The present invention relates to a patient mountable robot that will help a physician to reach a point of interest in a patient's body, and in particular, during an MRI or CT guided intervention in which the patient is inside a bore of a scanner. In such a configuration it is difficult to reach, for example, the patient's joints for arthrography or other similar procedure. Thus, the patient mountable robot is intended to reduce trial and error, increase precision for a needle placement, and be low cost compared to conventional large and bulky robots.

II. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Hypertrophic Arthrography is the evaluation of joint condition using imaging modalities such as computed tomography (CT) and magnetic resonance imaging (MRI). The average American child between the ages of 5-14 will experience one sports-related injury during that time period. A significant portion of these injuries involve internal derangements of shoulders, hips, wrists, and other joints. Magnetic resonance (MR) arthrography is the modality of choice for evaluation of suspected derangement of articular labral structures, untreated congenital joint dysplasias, articular cartilage, and other internal structures of the joint since it has higher soft tissue contrast in comparison to other modalities. Currently, arthrography requires two separate stages, an intra-articular contrast injection guided by fluoroscopy or ultrasound followed by an MRI. The inability to leverage the imaging capabilities of the MRI itself and the manual nature of needle placement lead to increased cost, anxiety, and in some cases prolonged sedation time, especially for the youngest and most anxious patients. Moreover, while the MRI could also be used for guiding the needle placement, patient access in the MRI can be difficult, especially for closed bored scanners. Therefore, the development of a small, body mounted robot to assist in needle placement in the MRI environment could streamline the procedure.

The conventional two-step workflow can result in anxiety for the patient, prolonged sedation time when sedation is needed for younger patients, radiation exposure from the fluoroscopic imaging, and may increase cost due to the use of both the fluoroscopy and MRI suite. In typical manual interventions, the physician guides the needle using cross-sectional images to reach a desired position in a joint space or near a bone. Traditional needle manipulation often requires multiple passes to reach the target. In MRI guided interventions, patient access can be difficult, especially for closed bored scanners. Therefore, the procedure is performed in two steps; first the fluoroscopy-guided needle placement and infusion injection is done. In the next step, the patient should be moved to the MRI-imaging procedure immediately to make sure that the targeting point and infusion is correct and effective. Consequently, a need exists for a patient mountable robot that will help the physician do the entire procedure under an MRI or other scanner in a single operation. In particular, there is a need for a patient mountable robot that will also provide a stable guide for the needle and reduce the number of needle passes by providing a steady and precise needle holder, which will reduce the procedure time and avoid exposure to radiation by eliminating the fluoroscopy-guided needle placement, which will reduce trauma to patient and reduce the burden to the physician.

The high-strength magnetic field currently present in a clinical MRI environment makes developing MRI-compatible equipment a challenge. Nonmagnetic materials, MRI-compatible actuators (piezo motors, pneumatic and hydraulic actuators), optical encoders, and sensors are key elements of these robotic systems. A few research groups have reported related work in the field of patient mounted robots for percutaneous interventions. However, none of the conventional patient-mounted robots for percutaneous interventions address the above-noted shortcomings.

SUMMARY

A new MRI/CT compatible patient mountable robotic system is introduced which can provide better targeting, improved clinical workflow, and allow better access with cylindrical bore MRI scanners. Such a mechanical design results in a minimal height profile which is an important issue considering the small diameter of the MRI scanner's bore (typically 60 cm). Also, this patient mountable robot makes it possible to wrap most of the robot with a sterile drape to provide a cheap and easy solution for sterilization. A unique design of mounting legs enables the robot to sit on non-flat surfaces. While a primary clinical application for the robot is arthrography, other MRI image-guided needle placement procedures such as injection (e.g. facet joint injection), biopsy (e.g. lung, liver), and lesion ablation are also potential applications for this robot.

In one aspect of the disclosure, the robot device is intended to be used in interventional radiology procedures where minimally invasive access to a region of interest in the body is required. Specifically, the device pertains to needle based procedures such as arthrography. One precise application includes MRI guided interventions to minimize radiation dose in pediatrics. However, the device is broadly applicable to any imaging modality including CT, fluoroscopy, and ultrasound imaging. In addition, the device is usable in other needle based procedures both in adults and children, including biopsy, drainage, and ablations. Finally, the patient mountable design is compact and unlike an external positioning robot, there is no need to worry about patient movement between the robot and needle during the procedure.

These objectives, and others, are attained by the present invention described in this disclosure.

In an aspect of the disclosure a patient mountable robot includes a four link mechanism including four links that form a closed loop structure. The four links include a base link that includes a spherical joint. The four link mechanism provides two rotational degrees of freedom about the spherical joint for a needle that is configured to pass through the spherical joint. The patient mountable robot includes a first actuator attached to the four link mechanism that moves the four link mechanism to provide the first of the two rotational degrees of freedom. The patient mountable robot includes a second actuator attached to the four link mechanism that moves the four link mechanism to provide the second of the two rotational degrees of freedom. The patient mountable robot includes a first robot base through which the base link of the four link mechanism passes. The patient mountable robot also includes a third actuator attached to the first robot base that linearly translates the base link so that a translational degree of freedom is provided for the needle that is configured to pass through the spherical joint.

In an aspect of the disclosure, the patient mountable robot includes the four link mechanism being a four link parallel mechanism.

In an aspect of the disclosure, the patient mountable robot includes a second robot base. The first robot base is rotatable relative to the second robot base so that a third rotational degree of freedom is provided for the needle that is configured to pass through the spherical joint.

In an aspect of the disclosure, the patient mountable robot includes the second robot base including one or more adjustable legs each configured to be attached to a patient's body.

In an aspect of the disclosure, the patient mountable robot includes the one or more adjustable legs each including an adhesive pad.

In an aspect of the disclosure, the patient mountable robot includes the one or more adjustable legs each including a lock to lock a position of a respective adjustable leg.

In an aspect of the disclosure, the patient mountable robot includes a fourth actuator attached to the first robot base that rotates the first robot base relative to the second robot base.

In an aspect of the disclosure, the patient mountable robot includes the first, second, third, and fourth actuators each including a piezo motor.

In an aspect of the disclosure, the patient mountable robot includes the first robot base and the second robot base each including a curved contour. In addition, at least one of the first robot base and the second robot base includes a guide so that the first robot base is movable along the guide with respect to the second robot base.

In an aspect of the disclosure, the patient mountable robot includes an inner surface of the second robot surface including a gear track. The fourth actuator includes a gear that is movable along the gear track to rotate the first robot base relative to the second robot base.

In an aspect of the disclosure, the patient mountable robot includes the third actuator including a belt positioned between pulleys, so that actuation of the third actuator rotates the belt around the pulleys and moves a structure of the base link that is engaged with the belt to linearly translate the base link.

In an aspect of the disclosure, the patient mountable robot includes the four links including a link that is a guide for the needle, and the link that is a guide for the needle is attached to the base link through the spherical joint.

In an aspect of the disclosure, the patient mountable robot includes the four links including a link that is attached to the base link through two revolute joints.

In an aspect of the disclosure, the patient mountable robot is compatible with at least one of imaging modalities including magnetic resonance imaging (MRI), computed tomography (CT), fluoroscopy, and ultrasound imaging, so that the patient mountable robot leaves no artifact or distortion in an image of a target workspace within taken with the at least one of the imaging modalities.

In another aspect of the disclosure, a system includes an imaging scanner and the patient mountable robot. The patient mountable robot is configured to be mounted on a patient while the patient is inside a bore of the imaging scanner.

In yet another aspect of the disclosure, a process includes mounting a robot to a patient at a target area of a body of the patient for a procedure. The process includes moving the patient into a bore of an imaging scanner. The process includes obtaining a first image of the target area of the body with the imaging scanner. The process includes determining a target needle point for a needle of the robot and a skin entry point for the needle based on the first image. The process includes actuating the robot to align the needle along a line connecting the target needle point and the skin entry point, while the robot is mounted on the patient. The process includes inserting the needle that is aligned into the body of the patient, while the robot is mounted on the patient. The process includes obtaining a second image of the target area of the body with the imaging scanner to confirm that the needle is correctly placed. The process includes moving the patient out of the bore of the imaging scanner. The process also includes removing the robot from the patient.

In an aspect of the disclosure, the process includes the procedure including arthrography, or biopsy, or drainage, or ablation.

In an aspect of the disclosure, the process includes the robot being the patient mountable robot.

In a further aspect of the disclosure, a sterilizable patient mountable robot includes a disposable part of the robot and a sheet draped over a part of the robot other than the disposable part.

The foregoing paragraphs have been provided by way of general introduction, and are not intended to limit the scope of the following claims. The described embodiments, together with precise advantages, will be best understood by reference to the following detailed description taken in conjunction with the accompanying drawings.

BRIEF DESCRIPTION OF THE DRAWINGS

A more complete appreciation of the disclosure and the attendant advantages thereof will be better understood by reference to the accompanying drawings and the subsequent detailed description, where:

FIGS. 26(A) and 26(B) illustrate an axial MRI image of a human subject's shoulder after removing the robot, with FIG. 26(A) being a T1 weighted image, and with FIG. 26(B) being a T2 weighted image.

DETAILED DESCRIPTION OF THE ILLUSTRATIVE EMBODIMENTS

Figure 1:
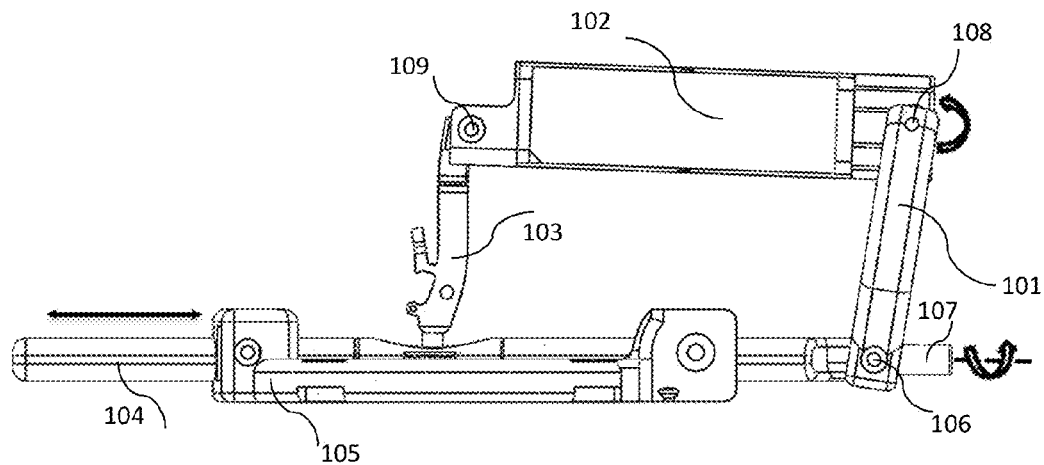
FIG. 1 illustrates a schematic of a 4-link parallel mechanism with a sliding base of one non-limiting illustrative embodiment of the invention.

Referring to the drawings, like reference numerals designate identical or corresponding parts throughout the several views.

One non-limiting illustrative embodiment of the invention is shown in FIGS. 1 to 6. FIG. 1 shows an overview of a 4-link parallel mechanism with a sliding base. This mechanism has three degrees of freedom (DOF), i.e., two DOFs for adjusting an orientation of a needle and one for translational motion. This parallel mechanism consists of four links 101, 102, 103, and 104. The base link 104 can slide back and forth which adds translational motion to the mechanism. Part 105 is the part that is fixed to a patient's body using adjustable mechanism which will be explained in more detail later. Part 105 has sliding holes in which the link 104 slides through these holes back and forth. The link 101 pivots with respect to the link 104 in two directions through shafts 106 and 107. The link 102 pivots with respect to the link 101 through shaft 108. The link 103 rotates with respect to the link 102 through shaft 109. The needle will be attached to the link 103. Therefore, the orientation of the needle and the link 103 is the same.

Figure 2:
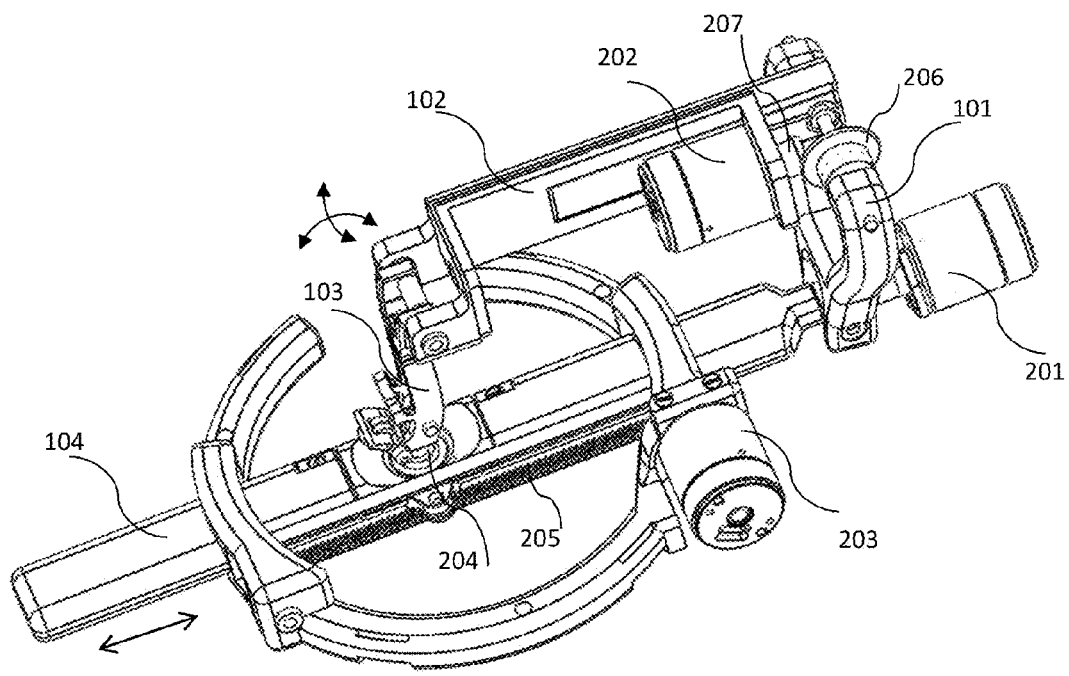
FIG. 2 illustrates a demonstration of locations of piezo motors in an assembled system.

Three piezo motors will be utilized to actuate the degrees of freedom. FIG. 2 shows the location of the piezo motors. Piezo motors 201 and 202 drive the 4-link parallel mechanism which adjusts the orientation of the needle. These piezo motors pivot the link 103 as well as the attached needle with respect to a spherical joint 204 in two directions. A third piezo motor 203 actuates the translational degrees of freedom. A time belt 205 is used to convert the rotation of the piezo motor 203 to the translational motion of the link 104. Bevel gears 206 and 207 transmit the rotation of the piezo motor 202 to relative rotation between the links 101 and 102.

Figure 3:
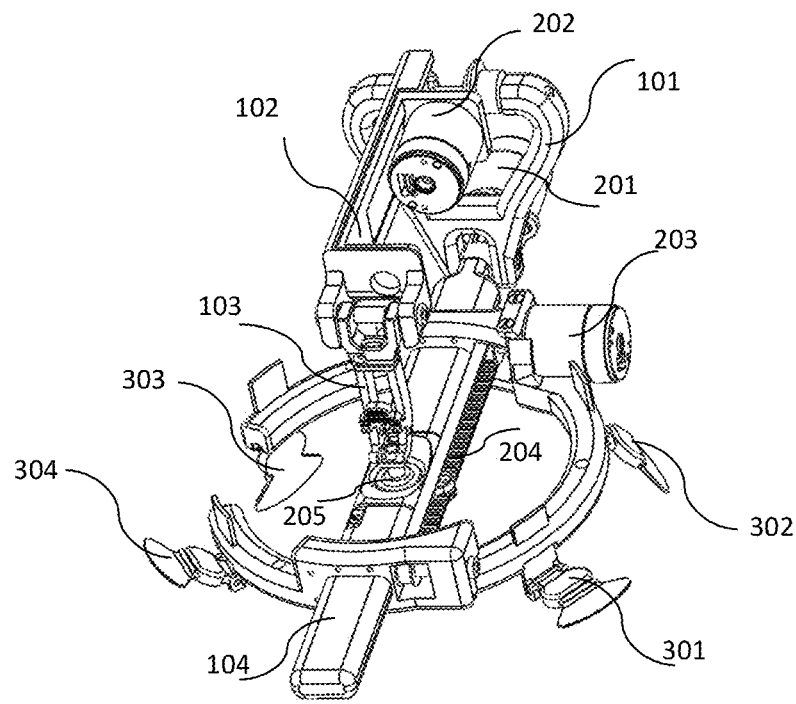
FIG. 3 illustrates locations of adjustable legs used to mount the robot on different patients in different locations.

To mount the robot to different patients having different sizes and in different interventional procedures, a four-adjustable-leg mechanism is developed. Each of the legs has three passive degrees of freedom which can fit patients of different shapes and sizes. FIG. 3 shows locations of the legs. Adhesive pads 301, 302, 303, and 304 are the parts of the legs which directly contact and stick to the patient's body.

Figure 4:
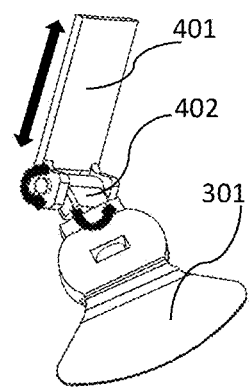
FIG. 4 illustrates a closed view of the adjustable legs.

FIG. 4 demonstrates the four-adjustable-leg mechanism and its passive degrees of freedom. This mechanism is adjustable for different heights and different shapes and slopes. Each of these legs has two adjustable rotational degrees of freedom about a joint 402 and one degree of freedom for adjusting the height of a leg 401. After adjusting the heights of the leg, this degree of freedom is lockable using an appropriate locking system.

Figure 5:
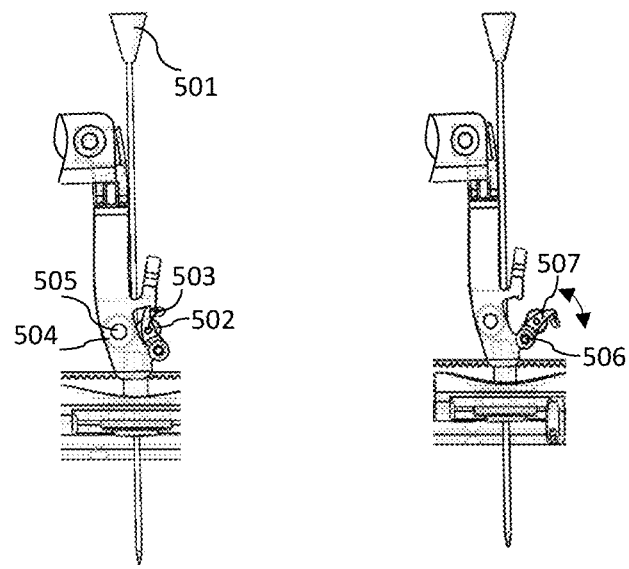
FIG. 5 illustrates a needle holding mechanism.

A needle holding mechanism is shown in FIG. 5. Two rolling parts 502 and 504 hold a needle 501. The rolling part 502 is rotatable through shaft 503 and the rolling part 504 is rotatable through shaft 505. The rolling part 502 is on an arm 507 and is pivotable around shaft 506 which make it possible to hold and release the needle 501.

Figure 6:
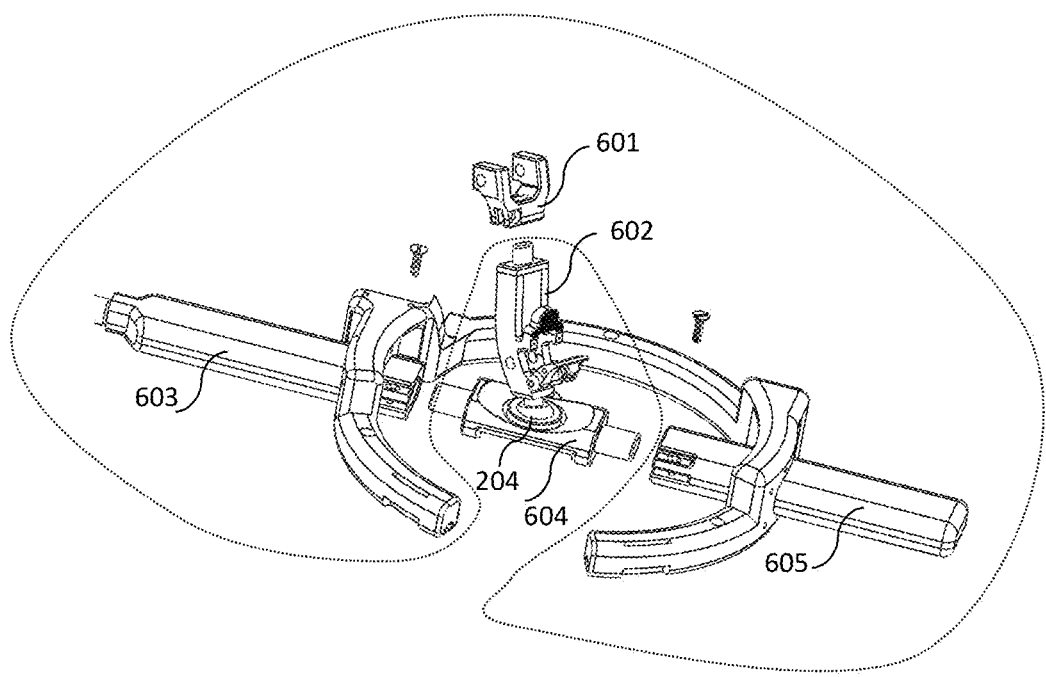
FIG. 6 illustrates how a sterilization problem is addressed by wrapping most of the parts with a protective sheet.

FIG. 6 illustrates a wrapping method of the robot for sterilization purposes. The link 103 is made of two different parts 601 and 602. The link 104 also consists of three subparts 603, 604, and 605. A protective sheet which is shown by a dotted line is used to wrap most parts of the robot including parts 601, 603, and 605. The parts 602 and 603 are disposable or sterilizable. Before each operation the robot is disassembled and a protective sheet is embedded as shown in FIG. 6 and then the robot is assembled again for the operation.

FIGS. 7 to 26 illustrate another non-limiting illustrative embodiment of a patient mountable robot according to the invention.

I. Mechanical Design

Figure 7:
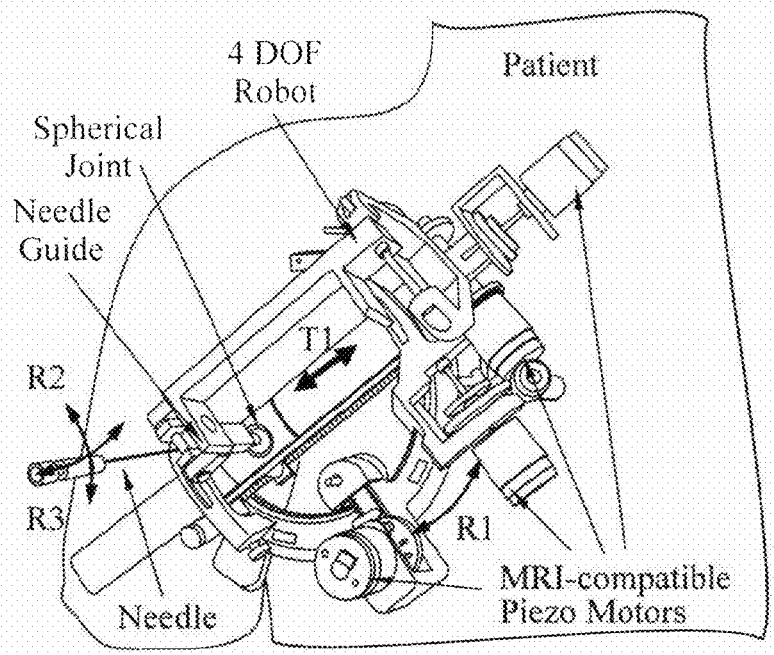
FIG. 7 illustrates a patient mountable robot of another non-limiting illustrative embodiment of the invention that includes four degrees of freedom (DOF).
Figure 8:
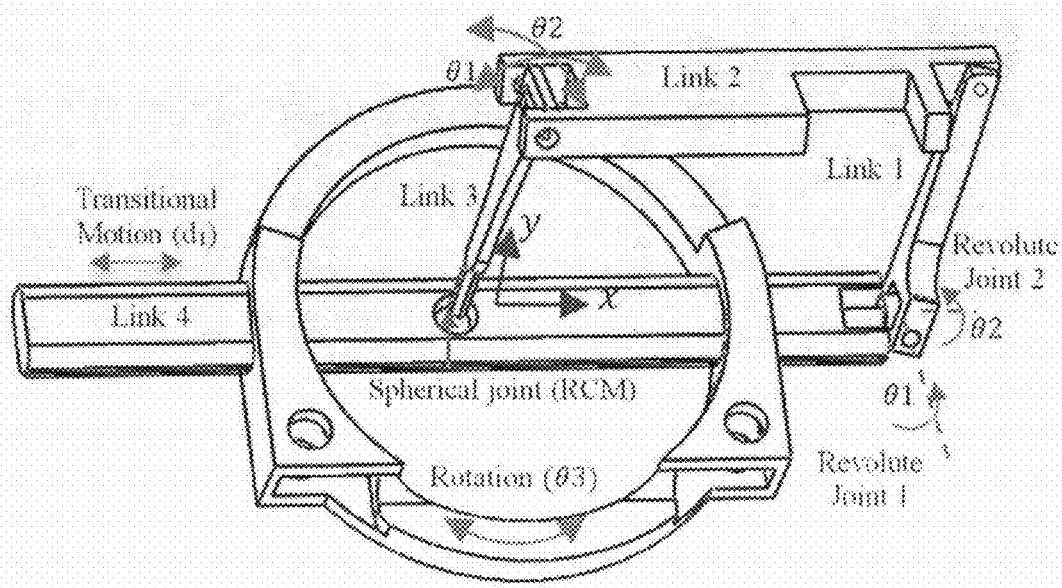
FIG. 8 illustrates a schematic of a 4-link parallel mechanism with a sliding base, and a rotatable base that holds the sliding base.

FIGS. 7 and 8 show a four-link parallel mechanism with a spherical joint that is a remote center of motion (RCM), yielding two rotational DOF about the spherical joint, R2 and R3 as shown in FIG. 7, or $\theta_1$ and $\theta_2$ as shown in FIG. 8, as well as two DOF for positioning a needle passing through a needle guide. The four-link parallel mechanism includes link 1, link 2, link 3, and link 4. A shaft between the link 1 and the link 2, and a shaft between the link 2 and the link 3, allow the four-link parallel mechanism to rotate in the $\theta_2$ direction. The spherical joint (RCM) between the link 3 and the link 4, and revolute joints 1 and 2 between the link 4 and the link 1, allow the four-link parallel mechanism to rotate in the $\theta_1$ direction in addition to the $\theta_2$ direction. The link 4, as a base of the four-link parallel mechanism, slides through a rotatable robot base to add a third DOF, T1 as shown in FIG. 7, or $d_1$ as shown in FIG. 8. The combination of this transitional motion with rotation of the rotatable robot base, R1 as shown in FIG. 7, or $\theta_3$ as shown in FIG. 8, provides maneuverability in an XY plane.

Figure 9:
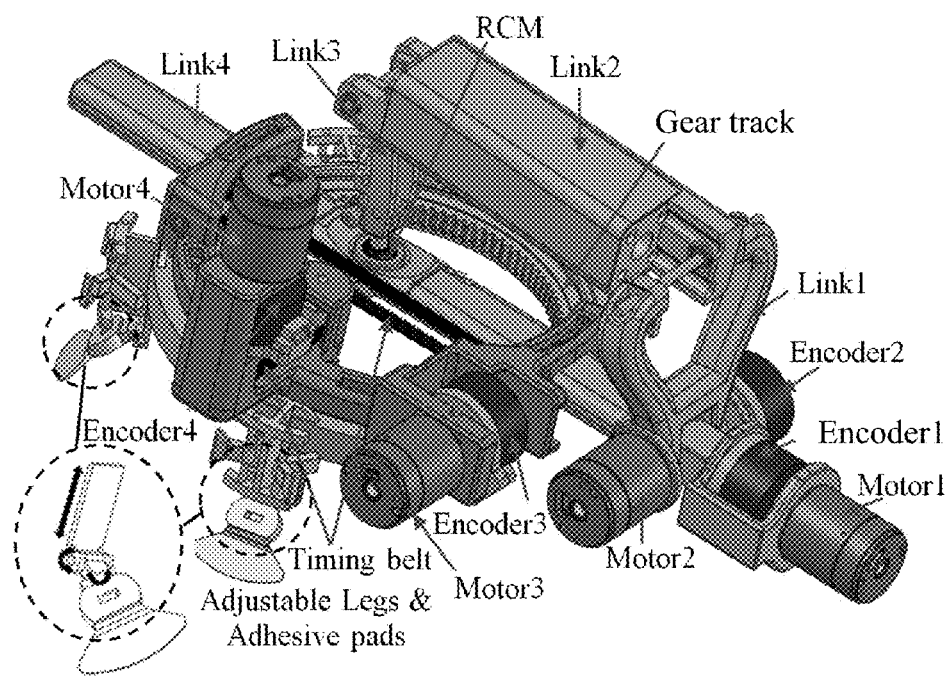
FIG. 9 illustrates a perspective view of a CAD model of the four DOF robot.
Figure 10:
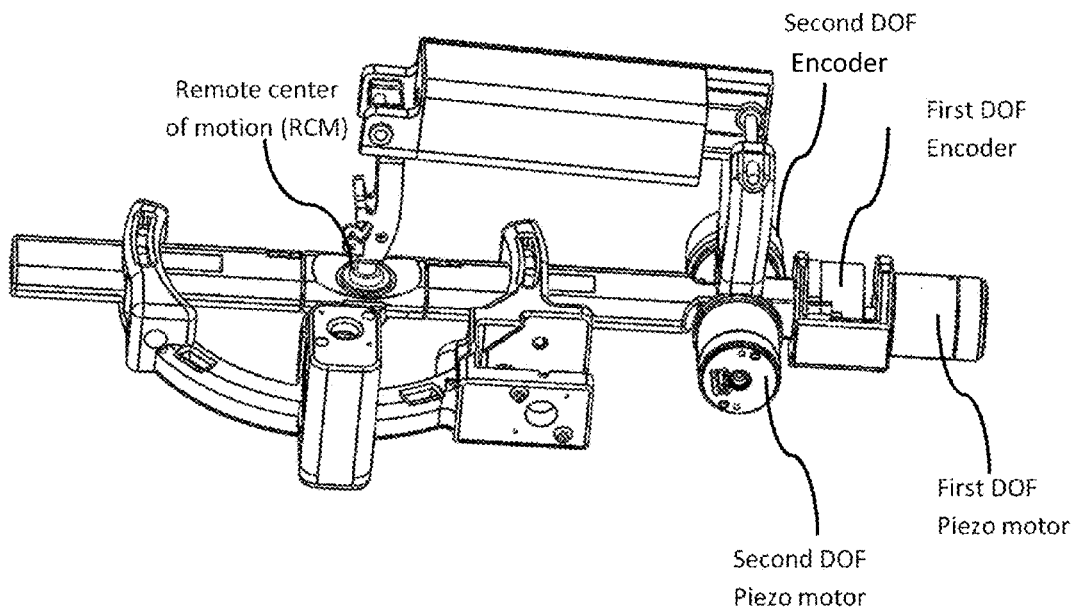
FIG. 10 illustrates a side perspective view of the 4-link parallel mechanism with the sliding base, and the rotatable base.
Figure 11:
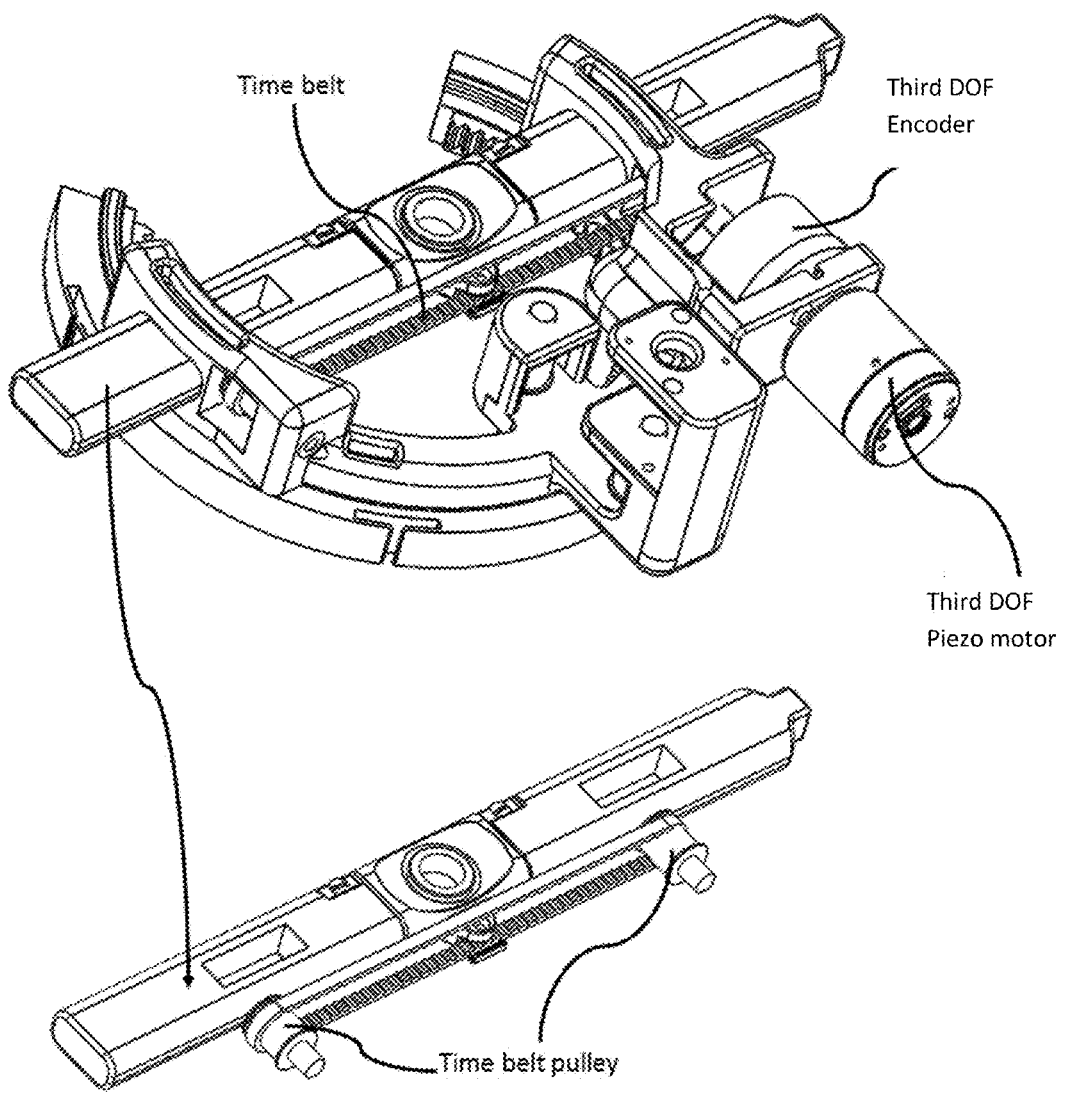
FIG. 11 illustrates a mechanism that produces sliding movement of the sliding base of the 4-link parallel mechanism.

As shown in a CAD model of FIG. 9, and in FIG. 10, motor 1 and motor 2 rotate the needle with respect to the spherical joint (RCM) to provide the two rotational DOF. The motor 1 and motor 2 each include an encoder. As shown in FIG. 9 and FIG. 11, a motor 3 that includes an encoder activates a mechanism including a timing belt and a pair of pulleys to slide the link 4 through the rotatable base. This provides the robot with translational motion along the link 4. Other mechanisms that provide the desired translational motion are also possible.

Figure 12:
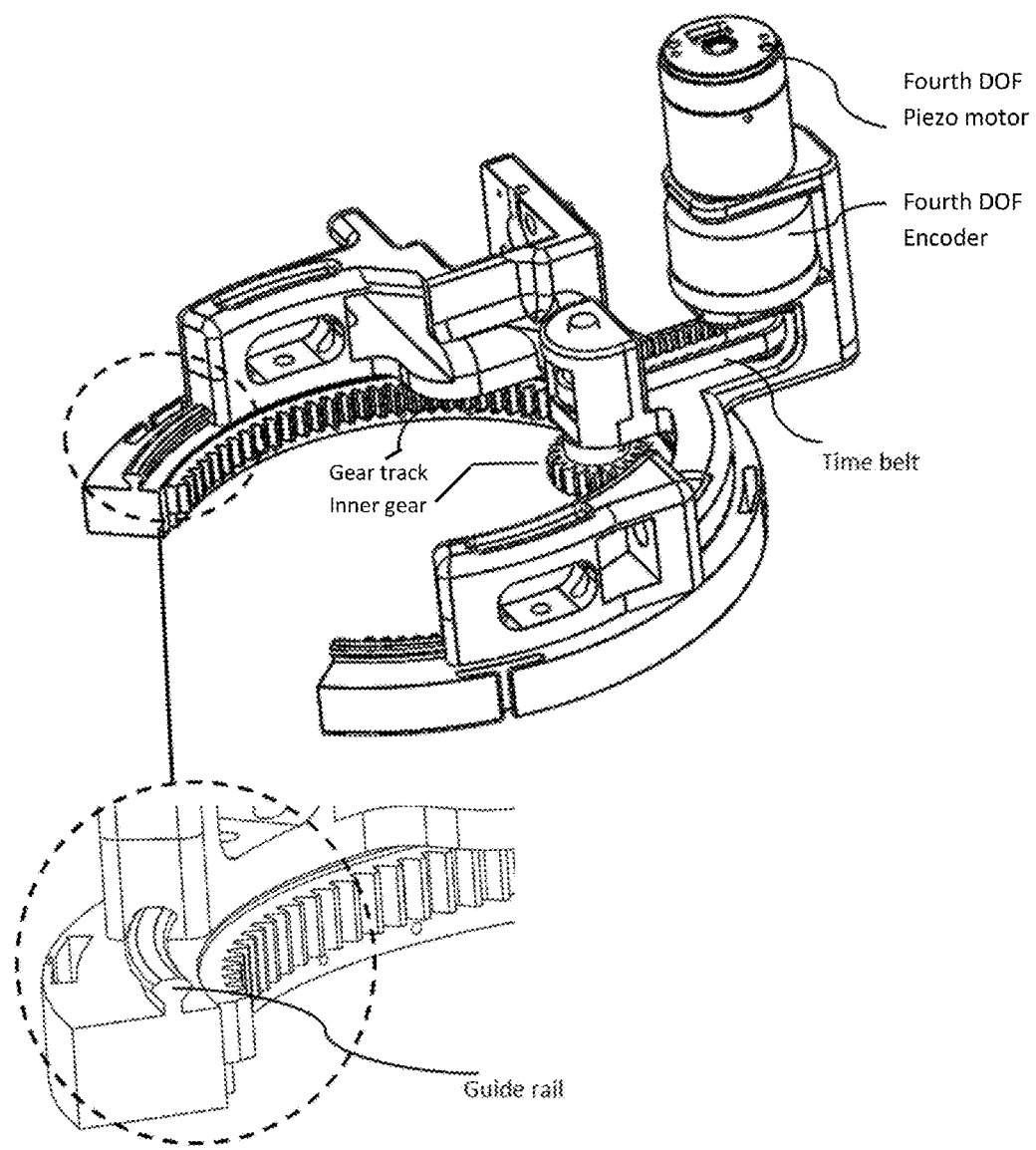
FIG. 12 illustrates the rotatable base positioned on a fixed base, and a mechanism that produces rotational movement of the rotatable base.

In FIG. 12, the rotatable robot base is shown in greater detail. The rotatable base, through which the link 4 slides, includes a motor 4 that includes an encoder. The motor 4 activates a mechanism including a time belt to rotate an inner gear. This inner gear engages with a gear track provided on a fixed robot base, so that the rotatable base rotates with respect to the fixed base. Other mechanisms that provide the desired rotational motion are also possible. The fixed base further includes a guide rail that engages with the rotatable base.

Figure 13:
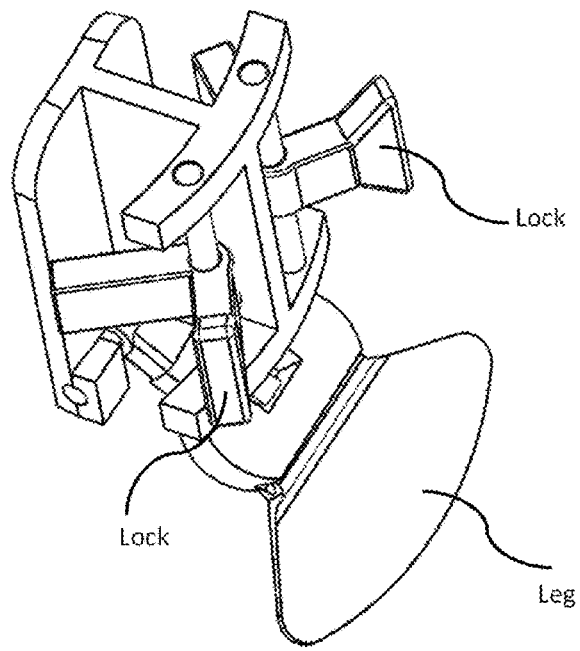
FIG. 13 illustrates another example of an adjustable leg and a locking mechanism of the adjustable leg.

FIG. 13 illustrates another non-limiting example of an adjustable leg and a locking mechanism of the adjustable leg. The leg may include one or more locks to lock the leg in position. The locks shown are pivotable. In addition, a support of the leg engages with the fixed robot base, as shown in FIG. 9, so that the fixed base is securable to a body part of a patient through the adjustable legs. The adjustable legs may also include adhesive pads.

Figure 14:
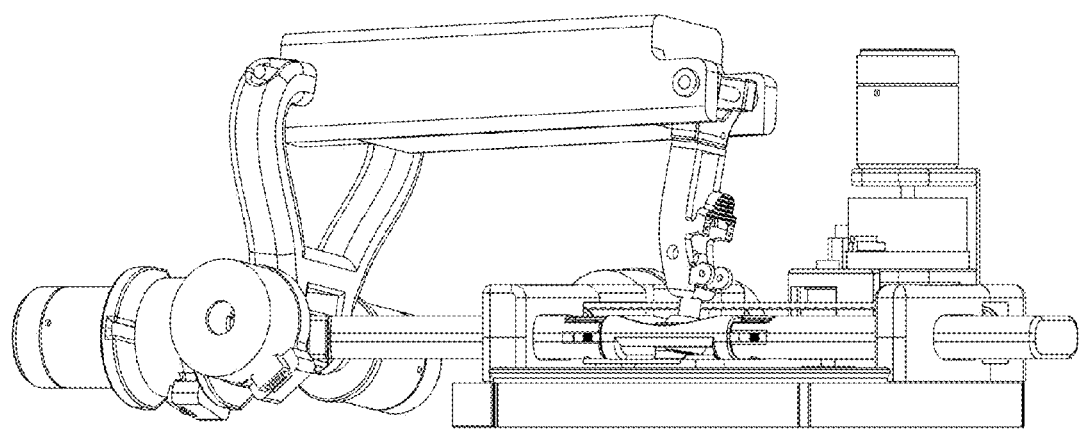
FIG. 14 illustrates a side perspective view of the four DOF robot.
Figure 15:
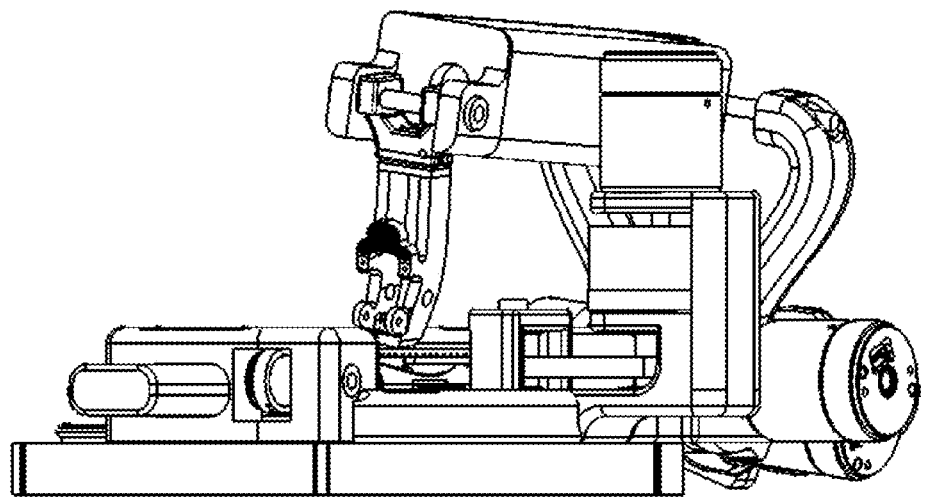
FIG. 15 illustrates a further side perspective view of the four DOF robot.
Figure 16:
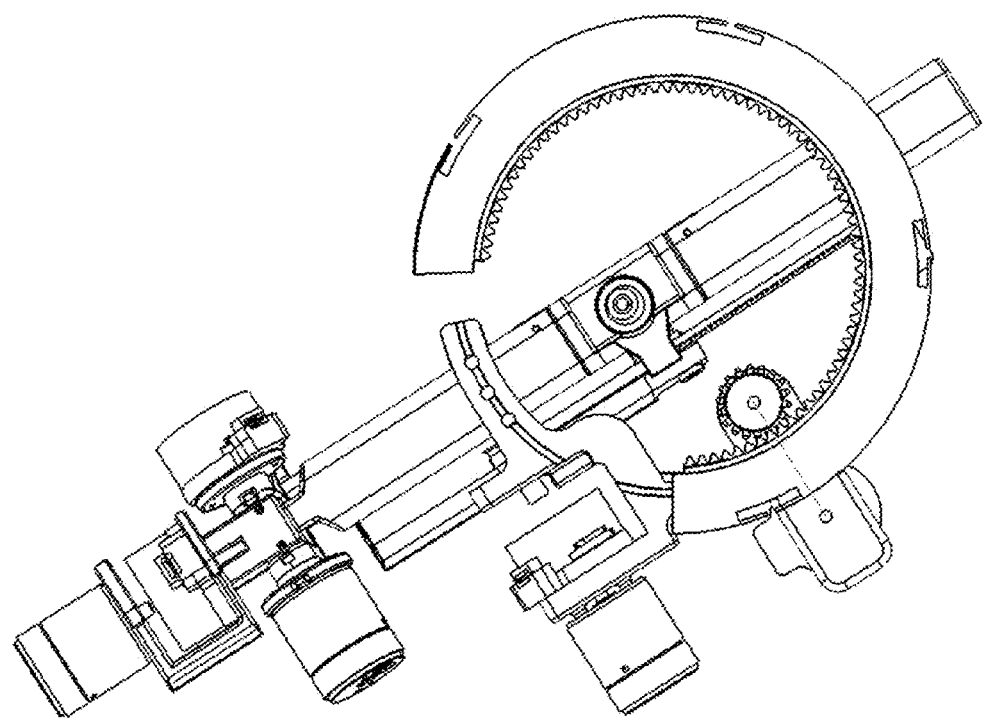
FIG. 16 illustrates a bottom view of the four DOF robot.
Figure 17:
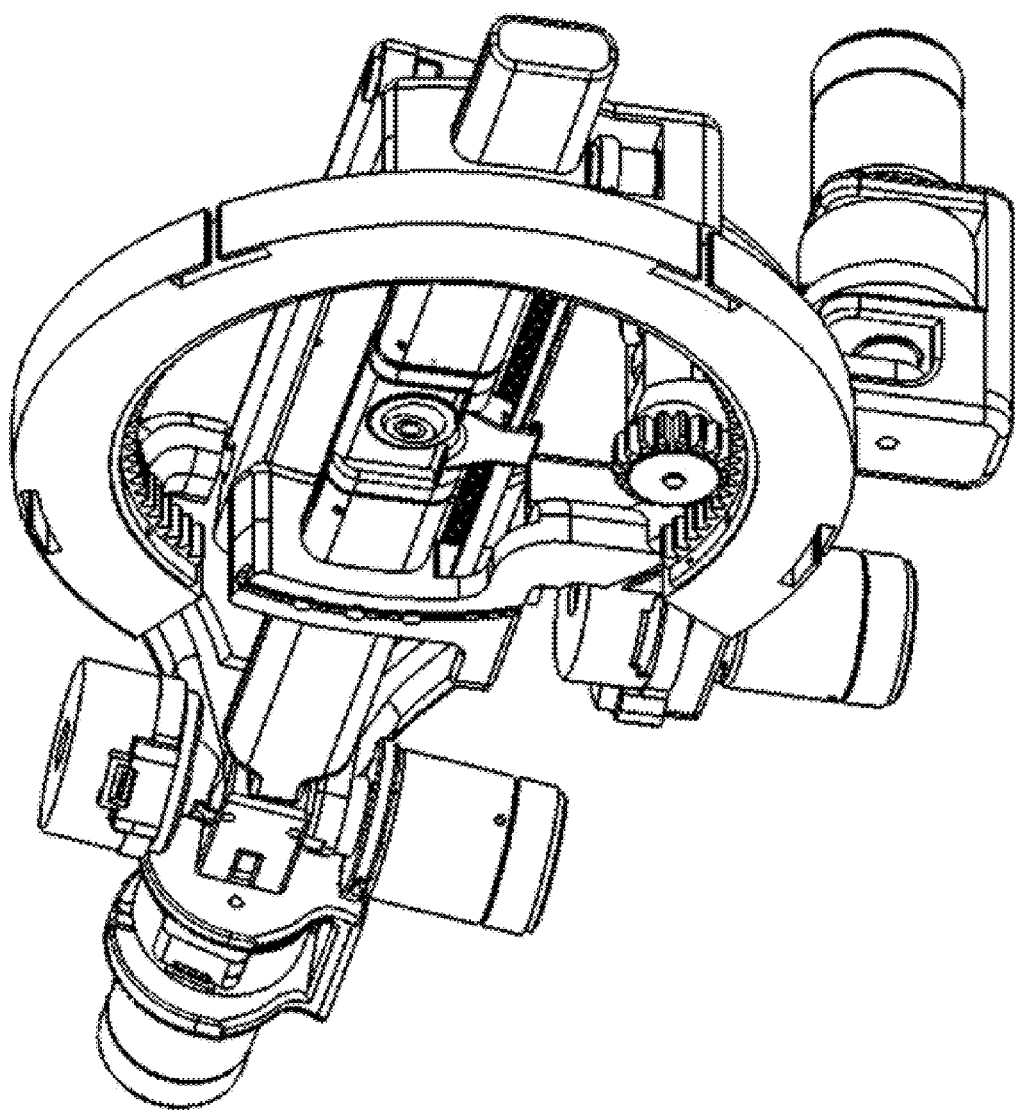
FIG. 17 illustrates a bottom perspective view of the four DOF robot.

FIGS. 14 to 17 illustrate the non-limiting four DOF patient mountable robot in various views to show greater detail. FIG. 14 shows a side perspective view of the four DOF robot. FIG. 15 shows a further side perspective view of the four DOF robot. FIG. 16 shows a bottom view of the four DOF robot. FIG. 17 shows a bottom perspective view of the four DOF robot.

The design requirements of this patient mountable robot include: a four DOF robot, with two DOFs for needle positioning and two DOFs for needle orientation, that is compact, rigid in structure, easily attachable to a patient's body, equipped with an adjustable mechanism to fit different size patients, easily sterilizable, MRI/CT safe and compatible, able to provide a simplified workflow while maintaining image quality, and able to provide a user-friendly interface. These criteria have been considered and are addressed as described below.

Four DOF robot: In typical interventional procedures, first a tomographic scan is performed and then a skin entry point is selected by a radiologist. This hand-eye calibration is done intuitively by the radiologist who requires a great deal of training. Based on the images and a deep understanding of the anatomy, the radiologist places, orients, and inserts a needle in a specific direction through the marked point on the skin to reach the target. For automating this procedure, four DOFs are required: two DOFs for moving the needle to reach the appropriate point on the skin; and two DOFs for orienting the needle along the line to the target.

Small size: The robot is designed to be mounted on the patient's body while he/she is inside an MRI scanner bore. The diameter of the scanner bore is typically 60 cm which limits the overall robot workspace. Therefore, the height profile of the robot is minimized. The overall dimensions of the robot are: 300 mm length, 130 mm width, and 100 mm height, although any dimensions allowing for adequate accommodation within a scanner are possible. The robot's workspace is a circular area of 10 cm in diameter for translational motion and +45° for rotational degrees of freedom for needle orientation, although other dimensions are also possible.

Rigid structure: The robot requires a rigid structure to avoid any error in needle placement. Errors may occur if the mechanism deforms while the needle is driven into the patient's joint. A parallel structure with an RCM is selected to make the robot small and rigid at the same time.

Ease of attachment: MRI/CT time is very expensive. In robotic assisted arthrography, the procedure time should be as short as possible. Therefore, the attachment of the robot is easy and fast. In this design, by using adhesive pads and/or tape, and/or other fixation medium, the robot is easily and quickly attached. The goal is to attach the robot to the patient's body in less than 3 minutes.

Adjustable mechanism: Due to the variation in patient size and different target joints in arthrography (shoulder, hip, elbow, etc.), the robot is adjustable for different situations. Four passive adjustable legs are part of the robot design, although any number of legs may be used. Each leg includes three DOF, although another number of degrees of freedom can be used, and each leg can be easily adjusted for different applications. Each leg includes an adhesive pad which sits and sticks on the skin of a patient's body.

Figure 18:
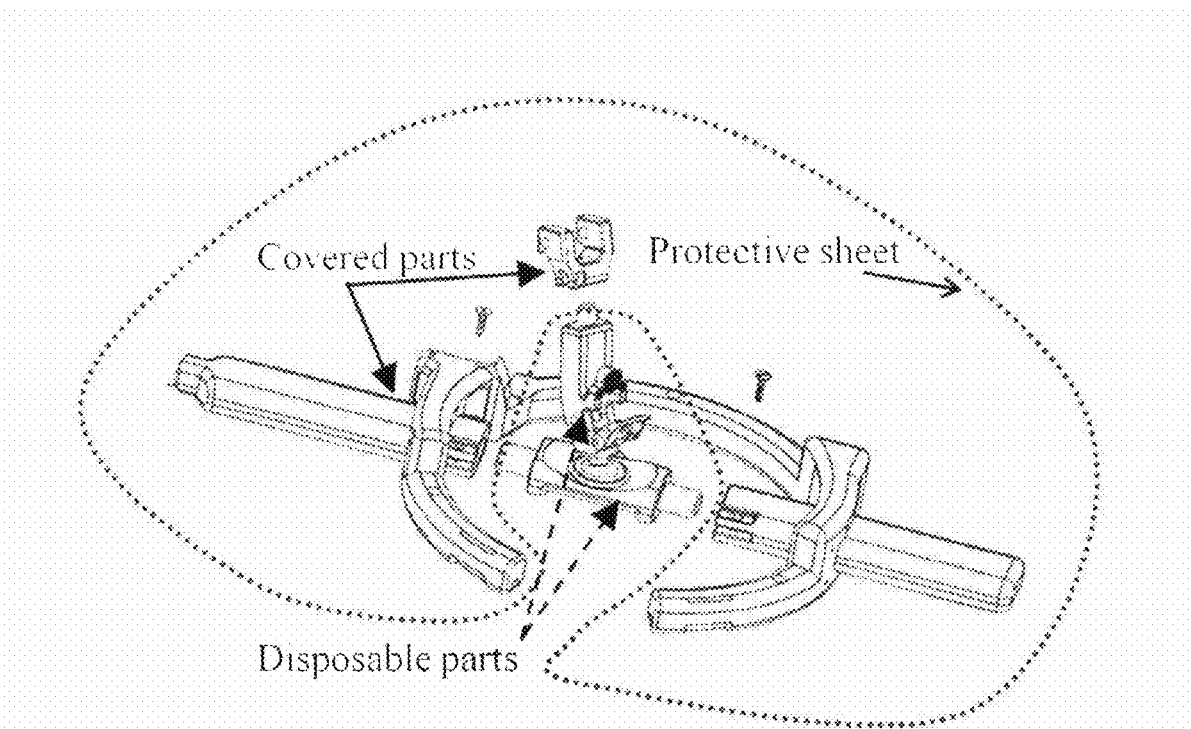
FIG. 18 illustrates another example of how the sterilization problem is addressed.

Ease of sterilization: For medical robotic systems, sterilization is a critical issue that must be addressed. Three possibilities include: 1) making the robot disposable, 2) using special material and sealing to make the robot sterilizable, and 3) covering the robot with an appropriate protective sheet to avoid exposure of the robot to the environment. Any one or combination of these methods can be incorporated with the robot. For example, a combination of these methods for sterilization is shown in FIG. 18. By separating the link 4 into three parts and the link 3 into two parts, it is possible to cover most parts of the robot with a protective sheet, and then assemble pieces of the links 3 and 4 together. The parts that are not covered can be either disposable or sterilizable.

MRI/CT safe and compatible: Ferromagnetic materials are hazardous in an MRI/CT room. Therefore, the robot is made of non-ferromagnetic materials, nonmagnetic actuators, and sensors. The robot is also MRI/CT compatible. Non-ferromagnetic metal parts can still cause artifacts in images. In a robotic assisted arthrography application where the robot sits directly above the imaging target, compatibility must be considered. Some experiments have been performed to investigate the MRI compatibility of the robot, particularly for a shoulder arthrography procedure, which are discussed later.

Simplified workflow while maintaining image quality: While a flexible coil is usually used for acquiring diagnostic images for shoulder arthrography, this coil may interfere with robot placement in robotic assisted arthrography. For the robotically assisted procedure, one option is to use a single coil which is placed under the robot or a custom made coil embedded with the robot's base. However, this coil may not give the high quality diagnostic images needed after contrast injection. Therefore, in a clinical workflow as described later, a spine coil built into the table is used for robot-to-patient registration, needle alignment, and insertion, without any flexible coil. A flexible coil is later utilized for obtaining diagnostic images after the robot is removed.

User-friendly interface: For control of the robot, two possibilities include: 1) a master-slave configuration, in which the physician can control the robot from an MRI control room with a standard joystick or with an MRI-compatible joystick from inside the MRI room; and 2) a positioning mode, in which the robot pre-aligns the needle into the desired trajectory automatically and the physician would then manually drive the needle to the target while the robot maintains the desired trajectory. The robot may operate under one and/or both of these user interfaces. The robot may include circuitry integrated into the robot or external to the robot to control operation of the robot. For example, the circuitry may execute an algorithm for pre-aligning the needle.

Figure 19:
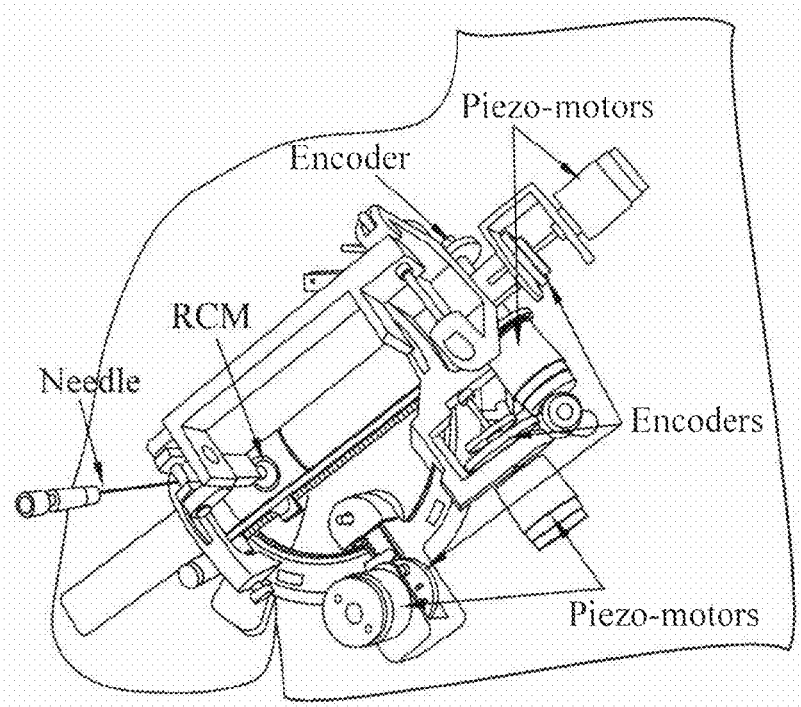
FIG. 19 illustrates a further view of the patient mountable robot mounted on a body.

FIG. 19 shows a non-limiting example of the robot made by a rapid prototyping machine (Objet 500, Stratasys) using Acrylonitrile Butadiene Styrene (ABS) material. MRI/CT compatible piezo motors (Piezo LEGS® Upsala, Sweden), and MRI/CT compatible encoders (E8P OEM Optical Kit Encoder, 512 CPR, US digital, Vancouver, Wash., USA) are used for actuation and measurement.

II. Robot Kinematics

Figure 20:
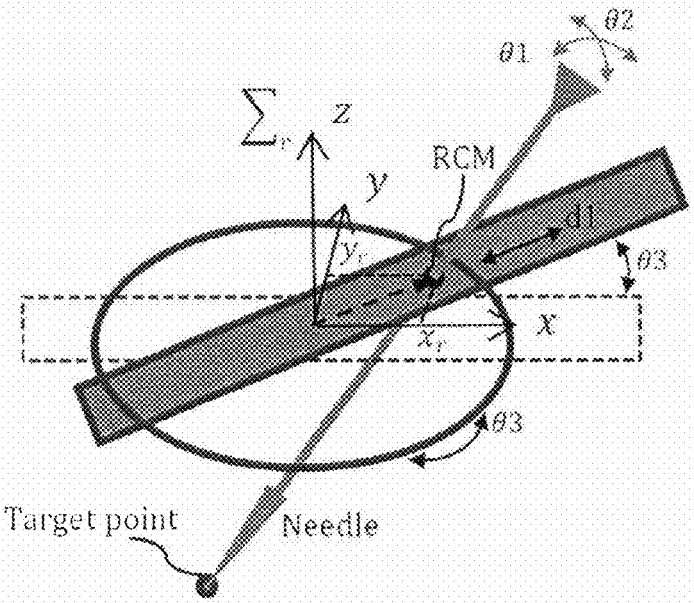
FIG. 20 illustrates a schematic diagram to show kinematics of a configuration of the robot.

In this section, kinematic equations for the robot are derived in a robot coordinate system. A transformation matrix from robot coordinate system to image coordinate system allows the physician to select the desired target point in the image and command the robot to align the needle towards the target. FIG. 20 shows the robot configuration and the parameters used to define the kinematics. The kinematic equations for this four DOF robot are as follows:

$$X_r = d_1 \cos(\theta_3) \quad (1)$$

$$y_r = d_1 \sin(\theta_3) \quad (2)$$

$$\alpha_r = \theta_1 \text{ and } \beta_r = \theta_2 \quad (3)$$

$$\begin{bmatrix} \dot{x}_r \\ \dot{y}_r \\ \dot{\alpha}_r \\ \dot{\beta}_r \end{bmatrix} = \overbrace{\begin{bmatrix} 0 & 0 & -d_1 \sin(\theta_3) & \cos(\theta_3) \\ 0 & 0 & d_1 \cos(\theta_3) & \sin(\theta_3) \\ 1 & 0 & 0 & 0 \\ 0 & 1 & 0 & 0 \end{bmatrix}}^{J} \begin{bmatrix} \dot{\theta}_1 \\ \dot{\theta}_2 \\ \dot{\theta}_3 \\ \dot{d}_1 \end{bmatrix} \quad (4)$$

where $X_r$ and $y_r$ are the translational components of the needle coordinate vector in the robot coordinate system ($\Sigma_r$), $\alpha_r$ and $\beta_r$ are the rotational components of the needle coordinate vector in the robot coordinate system. J is the Jacobian matrix.

III. Experiments and Results

The goals of the experiments performed were: a) to study distortions caused by the robot and piezo motors, and b) to investigate the possibility of using an embedded spine coil of the MRI scanner for needle placement in a shoulder joint. Each of these goals were addressed as follows:

A. Study of Distortions Caused by the Robot and Motors

Three different sets of images were obtained: 1) MRI images of a grating phantom, which is used as a ground truth, 2) MRI images of one piezo motor placed on top of the grating phantom, and 3) MRI images of the grating phantom with the robot placed on top.

Figures 21A, 21B:
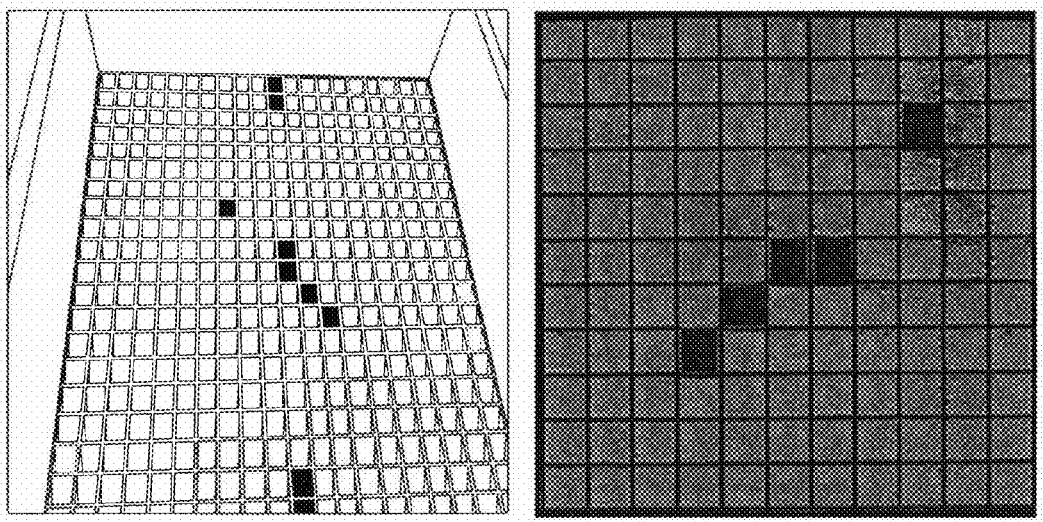
FIG. 21(A) illustrates a photograph of a grating phantom with 1 cm by 1 cm cubes.
FIG. 21(B) illustrates an MRI image of part of the phantom.

FIG. 21(A) shows a photograph of a grating phantom. An MRI image from a 1.5 Tesla Siemens scanner for this phantom is shown in FIG. 21(B). The cross lines in the image show any distortion caused by artifacts. In the FIG. 21(B) image there is no artifact or distortion since there is nothing on top of the phantom.

Figure 22A:
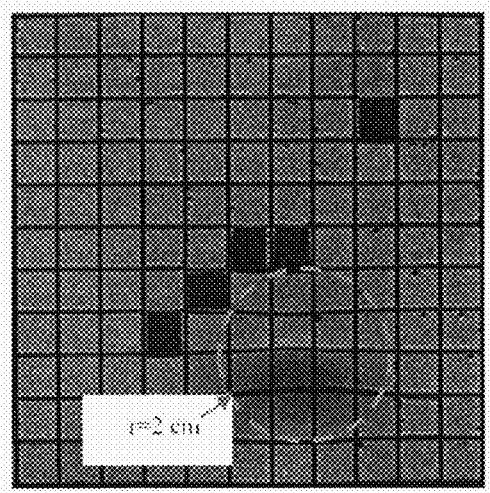
FIGS. 22(A) and 22(B) illustrate MRI images of the grating phantom when a piezo motor is placed at an isocenter on top of it, with FIG. 22(A) including a coronal plane under the motor, and with FIG. 22(B) including a coronal plane closer to the grating phantom.
Figure 22B:
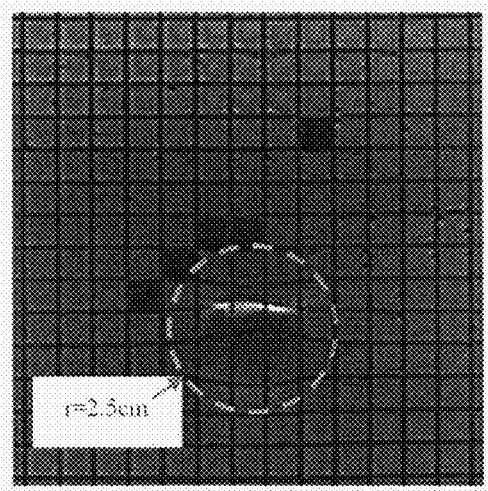

In a next step, the distortions due to the actuators were studied. One of the piezo motors was placed on the top of the grating phantom and new images were acquired. FIGS. 22(A) and 22(B) show the results in two different coronal planes. FIG. 22(A) shows a coronal plane under the motor. FIG. 22(B) shows a coronal plane closer to a surface of the grating phantom.

As shown in these figures a maximum distortion can be measured in FIG. 22(B). By investigating the images, it is determined that the artifacts caused by the piezo motors result in a 2.5 cm distortion in the image in all directions. This result means that with appropriate mechanical design, distortion on the images can be avoided by placing the motors at least 2.5 cm away from the targeting area.

Figure 23A:
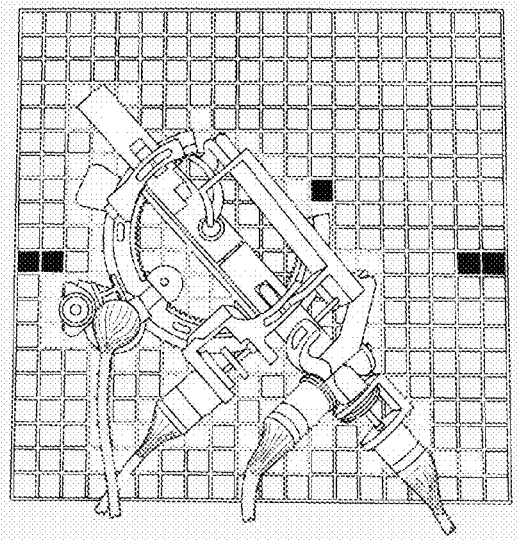
FIG. 23(A) illustrates a photograph of the robot with motors on top of the grating phantom.
Figure 23B:
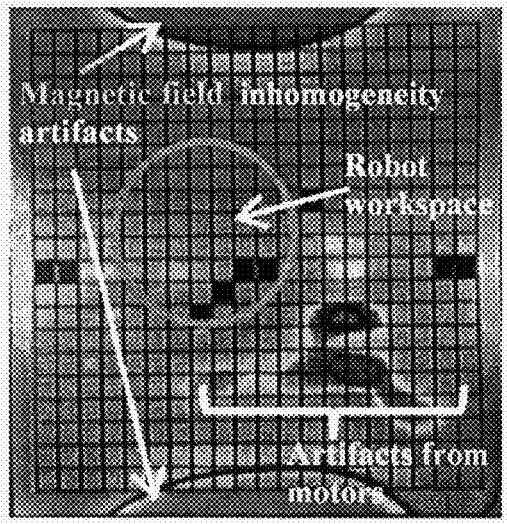
FIG. 23(B) illustrates an MRI image showing artifacts seen outside a robot workspace.

In a next step, the robot with motors attached was placed on top of the grating phantom and a new set of images were acquired. FIG. 23(A) shows the robot on top of the grating phantom and FIG. 23(B) shows an image obtained in this experiment in the coronal plane. As shown in FIG. 23(b) there is no distortion or artifact in the workspace of the robot. The robot is mostly made of ABS, which is a plastic, and no artifacts are expected from plastics. Other materials that do not result in distortion or artifact in the workspace of the robot may also be used. The motors are also far enough away to not cause any distortion in the target image area.

B. Use of a Spine Coil for Targeting a Joint Space

In this section, use of the spine coil which is embedded into the MRI scanner table, instead of using a flexible coil or single-loop coil, is investigated. Using the embedded spine coil of the MRI scanner reduces a need to place a coil directly on the shoulder which could interfere with positioning of the robot. In the following experiments, two sets of MRI images obtained using the spine coil are compared.

These two sets of images are an MRI image of a human volunteer's shoulder with and without the robot on the shoulder. The purpose of this experiment is to show that the artifacts caused by the robot on the shoulder do not degrade the MRI images of the joint and that joint space targeting is still possible.

Figure 24:
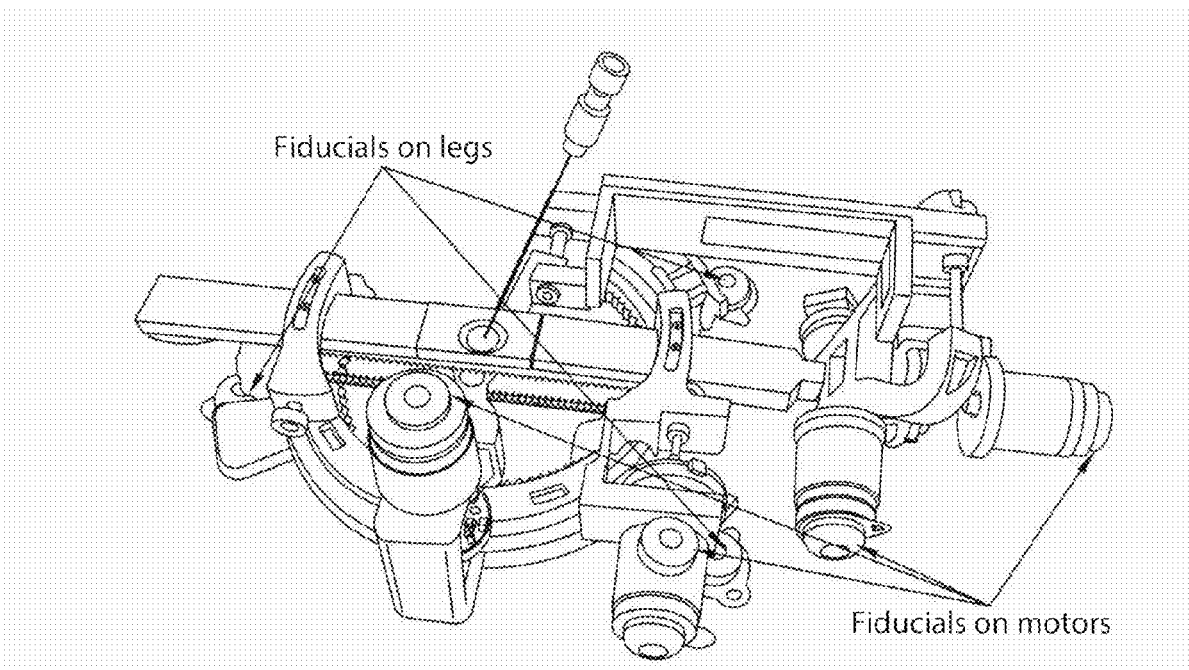
FIG. 24 illustrates the robot with fiducial markers.

Fiducial markers (Beekley Corporation, Bristol, Conn., USA) were attached to the robot on the piezo motors and on the robot legs. FIG. 24 shows the robot with fiducials. The robot was placed on the shoulder of the human volunteer and images were acquired using the spine coil in the MRI table. The following imaging parameters were used: a) T1 weighted image: SL4, TE 9.1 and TR 500, and b) T2 weighted image: SL4, TE 57 and TR 3300.

Figure 25A:
FIGS. 25(A) and 25(B) illustrate an axial MRI baseline image obtained by a spine coil showing a joint space with the robot on the shoulder, with FIG. 25(A) being a T1 weighted image, and with FIG. 25(B) being a T2 weighted image.
Figure 25B:
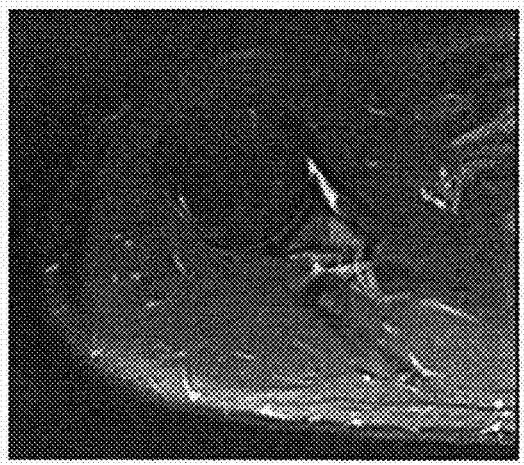

FIGS. 25(A) and 25(B) show respective T1 and T2 weighted axial MRI images of the shoulder joint space, while the robot was placed on the shoulder. These images were examined by an interventional radiologist. The radiologist confirmed that the artifacts caused by this shoulder mounted robot are negligible and should not affect the targeting of the joint for contrast injection.

To compare the images with and without the robot on the human subject's shoulder, the robot was removed from the shoulder and another set of images were taken without the robot on the shoulder. FIGS. 26(A) and 26(B) show axial MRI images of the shoulder after removing the robot from the shoulder. FIG. 26(A) shows the MRI image acquired using T1 signal weighting, and FIG. 26(B) shows the MRI image acquired using T2 signal weighting. Comparing FIGS. 26(A) and 26(B) with FIGS. 25(A) and 25(B), respectively, demonstrates that the robot is far enough from the target area and there is no noticeable artifact on the joint space area after attaching the robot to the patient's shoulder. It shows that the MRI images obtained by the spine coil in the presence of the robot are sufficient for the targeting of the joint space.

IV. Clinical Workflow

Figure 27:
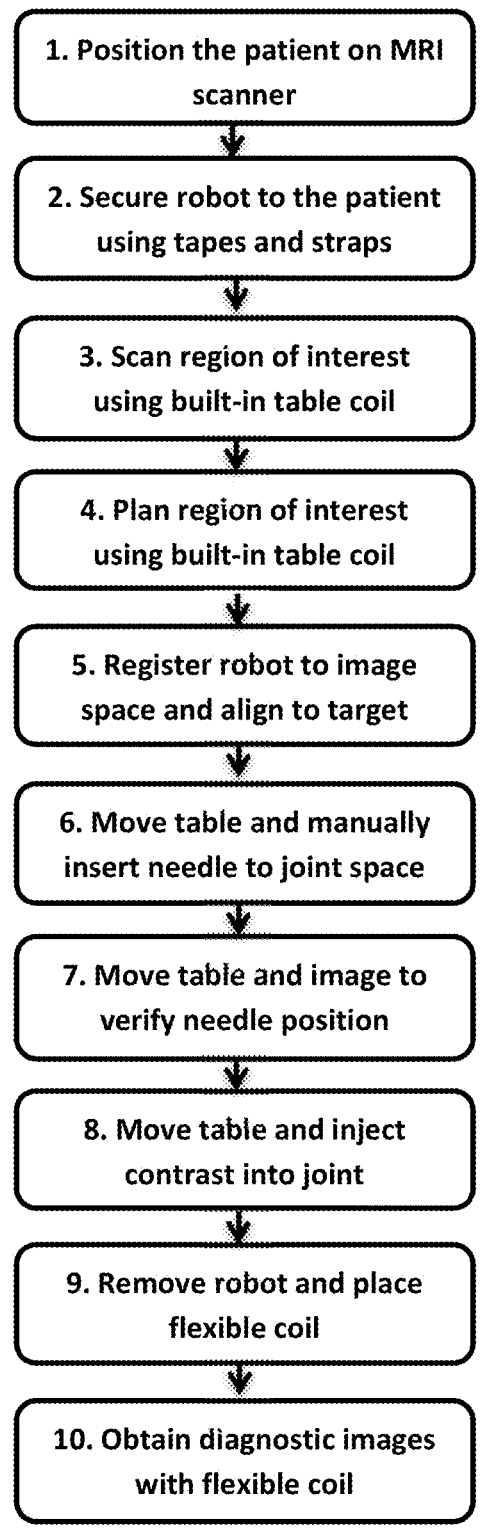
FIG. 27 illustrates a clinical workflow process according to a non-limiting illustrative embodiment of the invention.

A clinical workflow process according to a non-limiting illustrative embodiment is shown in FIG. 27. Although ten steps are included in the illustrative process, the process may include any number of steps.

In a Step 1, the patient is positioned in an imaging scanner for an imaging (MRI, CT, etc.).

In a Step 2, a patient mountable robot, such as one according to the invention, is attached to a patient's body based on a rough estimation of a target area. The target area may include a joint, such as a shoulder joint, or any other part of the body, such as on a lung, a liver, etc., where it is desired to perform a biopsy, a lesion ablation, a drainage, or other procedure. In the example of shoulder arthrography, the adjustable legs sit on top of the shoulder area. Using adhesive pads and/or tapes, the robot is securely positioned on the body.

In a Step 3, the patient is moved into a scanner bore. A first set of images is acquired using a spine coil built into the patient scanning table. Using passive fiducial markers incorporated into the robot's body, robot-to-patient registration is performed.

In a Step 4, based on the images, the radiologist will select a target needle point (e.g., the patient's joint space) and an entrance point on the skin.

In a Step 5, the robot is registered with an image space using the fiducials. The robot is then actuated to align a needle along a line connecting the skin entry point and the target point (e.g., a target point in the joint space).

In a Step 6, the patient is moved out of the scanner bore. The radiologist inserts the needle through a needle guide until the needle hits the target point (e.g., a bone in the joint space).

In a Step 7, to ensure that the needle is in a correct place, the patient is moved into the scanner to take confirmation images.

In a Step 8, the patient is moved out of the scanner to connect a syringe and to inject a contrast agent to the target point (e.g., to the patient's joint).

In a Step 9, the robot is removed from the patient's body. A flexible coil is then utilized for obtaining diagnostic images after the robot is removed.

In a Step 10, the patient is moved into the scanner for a last time to take the diagnostic images with the flexible coil.

In other non-limiting embodiments of the invention, MRI/CT compatible controller circuitry that operates the patient mountable robot according to an algorithm is envisioned. This controller would enable automatically driving a needle and injecting contrast during a real-time MRI/CT sequence, such as that for arthrography. A needle driver capability could also be adapted to other interventional procedures including MRI/CT. Other enabling technology such as force sensing, robot to scanner registration, and an MRI/CT compatible haptic device could also be incorporated with the patient mountable robot.

Additionally, systems, operations, algorithms, and processes in accordance with this disclosure may be implemented using controller circuitry including a processor/microprocessor or its equivalent, such as a central processing unit (CPU) or at least one application specific processor (ASP). The controller may utilize a computer readable storage medium, such as a memory (e.g., ROM, EPROM, EEPROM, flash memory, static memory, DRAM, SDRAM, and their equivalents), configured to store software that when executed by the controller, causes the controller to execute the systems, operations, algorithms, and processes in accordance with this disclosure. Other storage mediums may also be controlled via the controller, such as a disk controller which controls a hard disk drive or an optical disk drive.

The controller or aspects thereof, in an alternate embodiment, can include or exclusively include a logic device for augmenting or fully implementing this disclosure. Such a logic device includes, but is not limited to, an application-specific integrated circuit (ASIC), a field programmable gate array (FPGA), a generic-array of logic (GAL), and their equivalents. The controller may be a separate device or a single processing mechanism. Further, this disclosure may benefit from parallel processing capabilities of a multi-cored controller.

In another aspect, results of processing in accordance with this disclosure may be displayed via a display controller to a monitor that is peripheral to or part of the controller. Moreover, the monitor may be provided with a touch-sensitive interface to a command/instruction interface in an illustrative example. The display controller may include at least one graphic processing unit for improved computational efficiency. Additionally, the controller may include an I/O (input/output) interface, provided for inputting sensor data from sensors.

Further, other input devices may be connected to the I/O interface as peripherals or as part of the controller. For example, a joystick, a keyboard, or a pointing device such as a mouse may control parameters of the various processes and algorithms of this disclosure, and may be connected to the I/O interface to provide additional functionality and configuration options, or to control display characteristics. The actuators described in this disclosure, for example, may be connected to the I/O interface.

The above-noted hardware components may be coupled to a network, such as the Internet or a local intranet, via a network interface for the transmission or reception of data, including controllable parameters. A central BUS may also be provided to connect the above-noted hardware components together, and to provide at least one path for digital communication there between.

The foregoing disclosure describes merely illustrative embodiments of the present invention. As will be understood by those skilled in the art, the present invention may be embodied in other specific forms without departing from the spirit or essential characteristics thereof. Accordingly, the disclosure is intended to be illustrative of the present invention, but not limiting of the scope of the invention, as well as the following claims. The disclosure and any discernible variants of the teachings herein define, at least in part, the scope of the claim terminology, such that no inventive subject matter is dedicated to the public.

The invention claimed is:

1. A patient mountable robot, comprising:
   a four link mechanism including four links that form a closed loop structure, the four links including a base link that includes a spherical joint, and the four link mechanism provides two rotational degrees of freedom about the spherical joint for a needle that is configured to pass through the spherical joint;
   a first actuator attached to the four link mechanism that moves the four link mechanism to provide the first of the two rotational degrees of freedom;
   a second actuator attached to the four link mechanism that moves the four link mechanism to provide the second of the two rotational degrees of freedom;
   a first robot base through which the base link of the four link mechanism passes; and
   a third actuator attached to the first robot base that linearly translates the base link so that a translational degree of freedom is provided for the needle that is configured to pass through the spherical joint wherein the patient mountable robot is configured to be mounted on a patient and to provide a guided intervention while the patient is inside an imaging scanner.

2. The patient mountable robot according to claim 1, wherein the four link mechanism is a four link parallel mechanism.

3. The patient mountable robot according to claim 1, further comprising:
   a second robot base, and
   the first robot base is rotatable relative to the second robot base so that a third rotational degree of freedom is provided for the needle that is configured to pass through the spherical joint.

4. The patient mountable robot according to claim 3, wherein the second robot base includes one or more adjustable legs each configured to be attached to a patient's body.

5. The patient mountable robot according to claim 4, wherein the one or more adjustable legs each include an adhesive pad.

6. The patient mountable robot according to claim 4, wherein the one or more adjustable legs each include a lock to lock a position of a respective adjustable leg.

7. The patient mountable robot according to claim 3, further comprising:
a fourth actuator attached to the first robot base that rotates the first robot base relative to the second robot base.

8. The patient mountable robot according to claim 7, wherein the first, second, third, and fourth actuators each include a piezo motor.

9. The patient mountable robot according to claim 7, wherein the first robot base and the second robot base each include a curved contour, and at least one of the first robot base and the second robot base includes a guide so that the first robot base is movable along the guide with respect to the second robot base.

10. The patient mountable robot according to claim 9, wherein an inner surface of the second robot surface includes a gear track and the fourth actuator includes a gear that is movable along the gear track to rotate the first robot base relative to the second robot base.

11. The patient mountable robot according to claim 1, wherein the third actuator includes a belt positioned between pulleys, so that actuation of the third actuator rotates the belt around the pulleys and moves a structure of the base link that is engaged with the belt to linearly translate the base link.

12. The patient mountable robot according to claim 1, wherein the four links include a link that is a guide for the needle, and the link that is a guide for the needle is attached to the base link through the spherical joint.

13. The patient mountable robot according to claim 1, wherein the four links include a link that is attached to the base link through two revolute joints.

14. The patient mountable robot according to claim 1, wherein the patient mountable robot is compatible with at least one of imaging modalities including magnetic resonance imaging (MRI), computed tomography (CT), fluoroscopy, and ultrasound imaging, so that the patient mountable robot leaves no artifact or distortion in an image of a target workspace taken with the at least one of the imaging modalities.

15. A system, comprising:
the imaging scanner; and
the patient mountable robot according to claim 1, wherein the patient mountable robot is configured to be mounted on the patient while the patient is inside a bore of the imaging scanner.

16. A sterilizable patient mountable robot, comprising:
the patient mountable robot according to claim 1, wherein the patient mountable robot includes a disposable part of the patient mountable robot and a sheet draped over a part of the patient mountable robot other than the disposable part.

* * * * *